United States Patent [19]

Dougherty, Steven J.

[11] Patent Number: 4,700,561

[45] Date of Patent: Oct. 20, 1987

[54] APPARATUS FOR MEASURING ENTRAINED GAS-PHASE CONTENT IN A LIQUID

[76] Inventor: Dougherty, Steven J., 18310 17th St., E., Sumner, Wash. 98390

[21] Appl. No.: 832,365

[22] Filed: Feb. 24, 1986

[51] Int. Cl.$^4$ .............................................. G01N 7/00
[52] U.S. Cl. ........................................ 73/19; 73/61 R
[58] Field of Search .................. 73/61 R, 19, 61.1 R, 73/863.85, 863.83, 863.84, 863.86

[56] References Cited

U.S. PATENT DOCUMENTS

| | | | |
|---|---|---|---|
| 2,138,141 | 11/1938 | Cromer et al. | 73/19 |
| 3,726,143 | 4/1973 | Enarsson | 73/863.83 |
| 3,731,530 | 5/1973 | Tanguy et al. | 73/61 R |
| 3,911,256 | 10/1975 | Jones | 73/61.1 R |
| 4,120,192 | 10/1978 | Williamson | 73/19 |
| 4,164,137 | 8/1978 | Williamson | 73/19 |
| 4,269,064 | 5/1981 | Johnson et al. | 73/863.84 |
| 4,329,869 | 5/1982 | Toda | 73/19 |
| 4,365,505 | 12/1982 | Holzl | 73/19 |
| 4,565,085 | 1/1986 | Grgic et al. | 73/19 |
| 4,581,934 | 4/1986 | Holzl | 73/19 |

Primary Examiner—Stewart J. Levy
Assistant Examiner—Hezron E. Williams
Attorney, Agent, or Firm—Keith D. Gehr

[57] ABSTRACT

A method and apparatus for determining entrained gas-phase content of process streams comprising collection, isolation, and compression of a process sample, measurement of the compressive behavior, and calculation of the volume of entrained gas-phase by means of a thermodynamic equation of state. The sample is collected in a cylinder between a piston and a sealing plate. An actuator rigidly mounted on the piston force a piston rod into the contained sample where any gas phase is compressed. A pressure transducer measures change in pressure and another transducer measures linear travel of the piston rod to give information on volume change of the sample. The actuator travels with the piston at it is reciprocated by a first actuator to draw in or expel a sample. The apparatus is well adapted for automatic on-line measurement. A microprocessor operated control system for automatic operation is described.

8 Claims, 2 Drawing Figures

APPARATUS FOR MEASURING ENTRAINED GAS-PHASE CONTENT IN A LIQUID

BACKGROUND OF THE INVENTION

1. Field of the Invention

This invention relates generally to the measurement of gas phase entrained in process streams comprised of a liquid phase or a liquid phase containing suspended solid material.

2. Description of the Prior Art

Some of the prior art used for laboratory measurements of entrained air in process streams utilizes direct measurement by expansibility of isolated process stream samples subjected to reduced pressure. See, for example:

J. D. Boadway, "Gas in Papermaking Stock," Pulp and Paper Magazine of Canada, Convention Issue, Vol. 57, No. 3, 1956, pp. 185-189, 194.

E. Parker Troland, "Measuring Suspended Air in Paper Stock," Tappi, Vol. 49, No. 9, September 1966, pp. 100A-102A.

P. Landmark, "New Apparatus for Determining Entrained Air in Pulp Suspensions," Norsk Skogind., Vol. 21, No. 12, December 1967, pp. 503-506.

E. Barkowski, "Air in Aqueous Stock Suspension-Methods for Determining Air Content," Papiermacher, Vol. 28, No. 3, Mar. 18, 1978, pp. 44-46.

All of these methods provide a direct measurement of the entrained air content by means of collection and isolation of a sample, subjection of the sample to reduced pressure, measurement of the expansion of the sample due to the expansion of the entrained gas phase, and, by means of common thermodynamic equations of state, calculation of the fraction of sample which is entrained gas phase.

An important observation about the prior art is that in neither these references, nor in any of the open literature, is mention made of compressing rather than expanding an isolated sample in order to measure its entrained gas-phase content. In addition, none of the apparatus disclosed in the prior art is capable of compressing an isolated sample. Furthermore, none of the prior art is capable of providing on-line automatic process measurements due to a number of factors, including for example, fragile construction, pluggage with particulate material, and leakage of sealing valves.

The present invention describes the determination of the entrained gas-phase content of process streams by means of the compression of process samples, and also describes an apparatus which automatically provides direct and on-line entrained gas-phase measurement using compression of process samples rather than expansion of process samples.

SUMMARY OF THE INVENTION

The practice of determining the entrained gas-phase content of process streams by means of collection, isolation, and compression of process samples is taught by example in the description of an apparatus for taking such measurements.

The first consideration of the apparatus is to subject the sample to pressure, rather than vacuum. To avoid the problem of pluggage, the second consideration is to build the sampling device of large-diameter cross section, free of obstructions and constrictions, providing no interruption of any of the process flows. The third consideration is to make the device fully automatic.

The process sample is periodically withdrawn from any convenient location in the process using a piston and cylinder mechanism, and is isolated at the same pressure as the process fluid. If an external stream is first taken from the process, and the apparatus samples this external stream, then the isolated sample can be obtained at pressures different from the process pressure. Such a sampling technique adds additional capabilities to the sampling apparatus such as, for example, the feasibility of determining dissolved gas content in high pressure systems by depressurizing a stream from the system and then measuring the entrained air which results due to reduced gas solubility at reduced pressures.

The isolated sample is then subjected to compression by mechanical action up to the desired final testing pressure. Any final testing pressure is acceptable within the limits of component integrity on the high side, and accuracy, relative to the initial pressure, on the low side. Final pressures in the range of 10-110 psig above the process pressure provide adequate accuracy while not requiring specialized high pressure construction.

The amount by which the isolated sample compresses while being subjected to the external pressure provides the measure of gas-phase volume in the process sample. For most gasses at moderate temperature and pressures, the ideal gas law is adequate to describe gas phase compressibility $$(P_1 V_1)/T_1 = (P_2 V_2)/T_2$$

When sampling and testing are done at the same temperature, the percent gas phase, PGP, relative to the sample volume, $V_s$, is given by $$PGP = P_2/(P_2 - P_1) \cdot (\Delta v)/V_s$$

where $\Delta v$ is the volume change in going from the initial pressure, $P_1$, to the final pressure, $P_2$, with both pressures measured on an absolute basis. In some embodiments, the isolated sample and pressurizing system will contain a small amount of dead volume, so that $\Delta v$ as measured will be adjusted by a dead volume correction before PGP is calculated.

In some processes, the gas phase will be highly non-ideal due to its chemical nature or to surface effects for very small entrained bubbles or for bubbles adsorbed on surfaces. In that case, alternate gas-phase equations of state can be applied.

DESCRIPTION OF THE PREFERRED EMBODIMENTS

Figure 1:
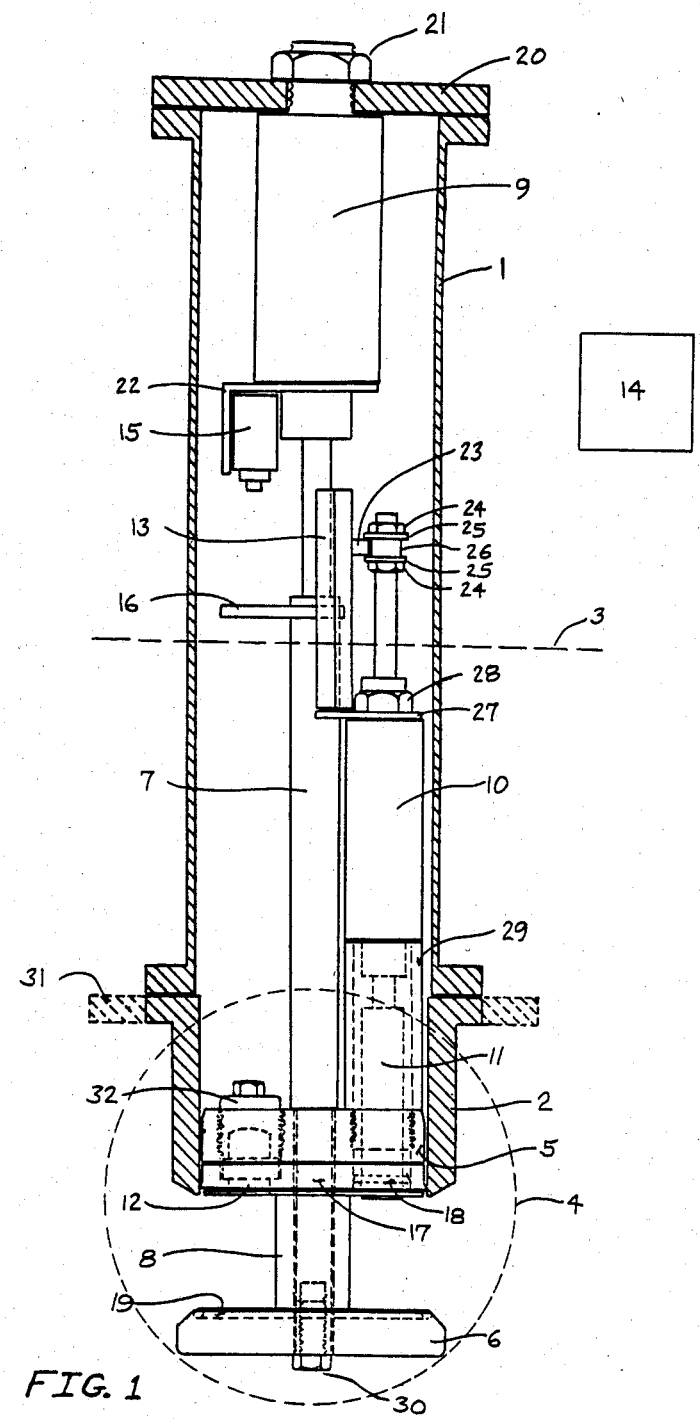
FIG. 1 is an open cross section of the apparatus.

Referring to FIG. 1, an embodiment of the apparatus is explained as follows:

Cylinder 1 provides the framework for the apparatus. Cylinder 2, attached by any convenient method to cylinder 1, provides a cavity for isolation of the sample, as presently described. Cylinders 1 and 2 are separate mechanical units in order to simplify servicing of the apparatus. It is evident that cylinders 1 and 2 could be a single integral unit.

Cylinder 1 is inserted into the process boundary, illustrated by dashed line 3 as in the case of a tank or vessel wall, or in the case of an open surface of process fluid contained in a vessel. Optionally, cylinder 1 may be inserted into a process pipe illustrated by dashed line 4. Optionally, pipe 4 may be a short section of pipe, isolated from the process, but accepting a sample flow from the process by means of a separate sample line. The actual method of mechanical attachment to the process is dependent upon the sampling mode: immersion in vessel, insertion in vessel, insertion in pipe, or isolated sample collection. An acceptable mechanical device for attachment to a pipe or vessel in the preferred embodiment is a flanged connection 31. In optional embodiments, flange 31 can be located at any convenient position along cylinder 1 or cylinder 2. The orientation of insertion of cylinder 1 is as required by the process. It is evident that the testing apparatus can function in any position—vertical, horizontal, upside down, etc.

To provide proper operation in particulate-containing process fluid, cylinder 2 is designed with a bevelled edge facing the process fluid, as shown. The flat portion of the bevelled edge increases the sealing force between cylinder 2 and O-ring 19 in sealing plate 6 when the pistons are in the retracted position. The sealing force is sufficient to deform O-ring 19 around any particulate material, thereby providing a seal even in the presence of particulate material.

Sample piston 5 and sealing plate 6 are rigidly connected and separated by piston rod 7, spacing bushing 8, and fastening bolt 30. Any spacing, for example 2 inches, providing sufficient sample for testing, may be used. Sealing plate 6 is significantly thicker than necessary for strength considerations, for example $\frac{3}{4}$ inch, and the edges are bevelled in order to reduce any tendency for solids in the process stream to tangle on the piston.

Actuator 9 is rigidly attached to the framework cylinder 1 by means of cap 20 and nut 21. Actuator 9 retracts piston 5, the outer face of which is initially flush with the outside end of cylinder 2, from the process fluid thereby forming a sample cavity bounded by the lower face of piston 5 and the inside wall of cylinder 2. The cavity thus formed collects the process sample. Sealing plate 6 follows piston 5 because of its rigid attachment thereto, thereby isolating the sample by means of the seal developed between the lower edge of cylinder 2 and O-ring 19. Actuator 10 which is rigidly attached to piston 5, by means of supporting member 29, then extends piston 11 into the sample cavity to generate pressure in the isolated sample. Transducer 12 measures the pressure and transducer 13 measures the displacement of piston 11. Transducer 12 is held in place in piston 5 by threaded follower 32. Transducer 13 is attached to actuator 10 by means of member 27 and nut 28. Transducer 13 is activated by movement of member 23 which is moved by its attachment to actuator 10 by means of nuts 24, washers 25, and spacer 26. In the preferred embodiment, transducer 12 is a diaphragm-isolated strain-gauge transducer and transducer 13 is a linear potentiometer. It is evident that transducer 12 could be an alternate device such as a non-isolated strain-gauge transducer or a transmitting bourdon tube pressure gauge, and transducer 13 could be an alternate device such as a rotational potentiometer with proper gearing or a linear variable differential transformer (LVDT).

The pressure generated is a function of the force produced by actuator 10. Any pressure which provides sufficient accuracy in the calculation of entrained gasphase is acceptable. A pressure of about 10 psi above the unpressurized isolated sample pressure provides sufficient accuracy. Higher pressures provide greater accuracy, but require more stingent mechanical design. Pressures of about 110 psi above the unpressurized isolated sample pressure do not cause unusual mechanical design problems while providing increased accuracy.

The pressure and displacement signals are read by microprocessor 14, which calculates the percent gasphase and outputs a corresponding signal which can be used for process control. Actuator 10 then retracts piston 11, and actuator 9 extends the piston assembly into the process fluid for collection of another sample.

In the preferred embodiment, actuators 9 and 10 are pneumatic cylinders, although it is evident that alternate actuators such as electrical motors with appropriate gearing can also be used. Actuators 9 and 10 can also be combined into one unit.

Control over the timing of the movement of actuator 10 is effected by limit switch 15, which is rigidly attached to actuator 9 by means of member 22, and by limit tab 16, which is rigidly attached to piston rod 7. In the fully retracted position, limit tab 16 actuates limit switch 15, which then provides a signal to the automatic control logic. The use of this signal is explained in the description of FIG. 2, below. In the preferred embodiment, limit switch 15 is a pneumatic switch, although it is evident that an electrical switch will also perform the required function.

Seals 17, 18, and 19 provide the required isolation to avoid leakage during and between sampling periods and during the pressurization phase. In the preferred embodiment, seals 17 and 18 are standard hydraulic cylinder seals such as those sold by Garlock and Parker Corporation, Salt Lake City, Utah, and seal 19 is a standard O-ring. Seal material is as required for process compatability.

An option for generating pressure in the isolated sample is by means of addition of pressurized process compatible fluid into the sample cavity.

The minimum dimensions for diameter and length of cylinder 1 are constrained by space required for the actuators, transducer, and position sensor. The maximum dimensions for diameter and length of cylinder 1 are unlimited, but are practically constained by cost, handling, and installation considerations. A 4-inch diameter and a 20-inch length have been found to allow sufficient working space while optimizing other factors. Obviously, both larger and smaller dimensions can be used.

Figure 2:
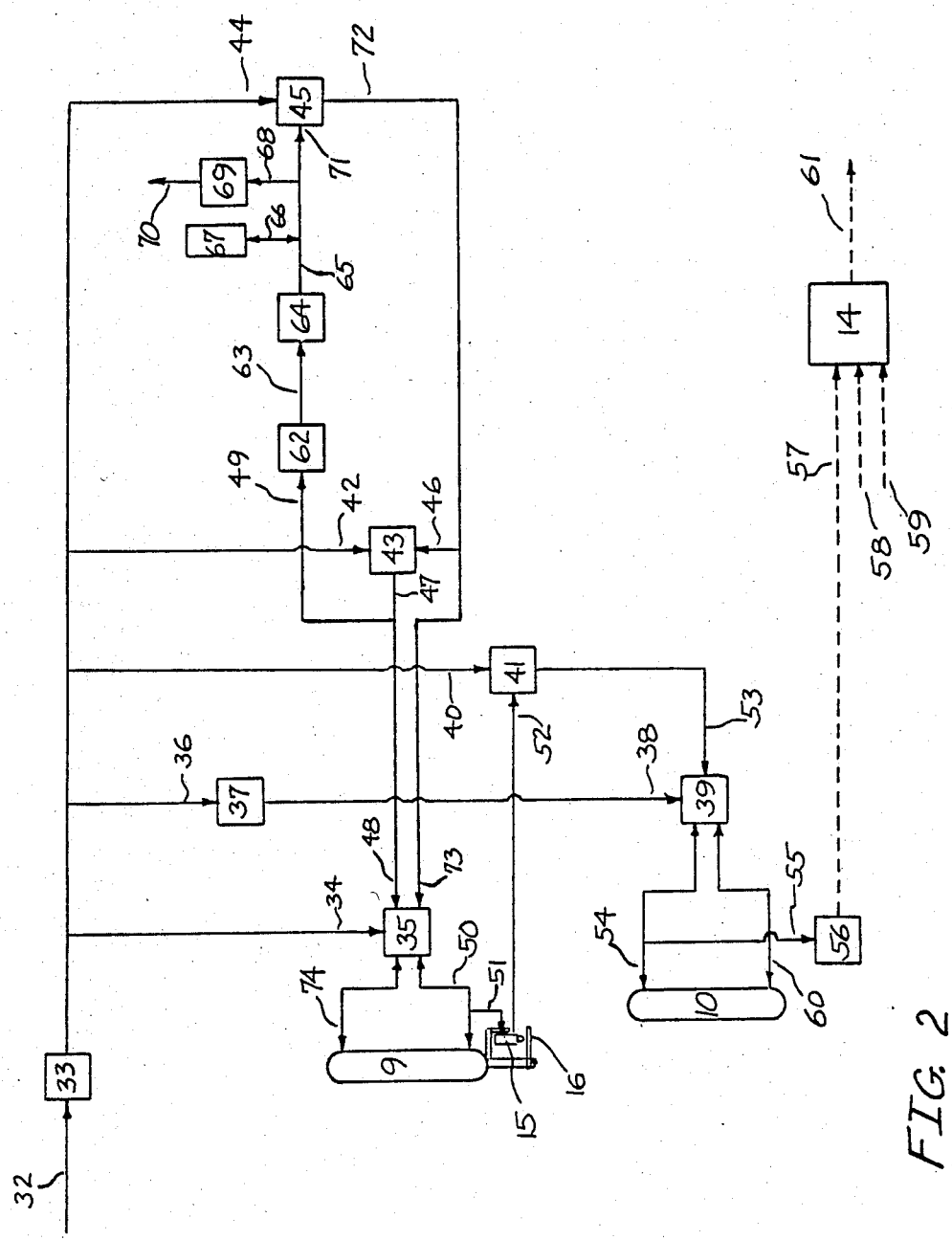
FIG. 2 is a schematic diagram of the system providing for automatic operation.

FIG. 2 is a diagram of the control logic for the sampling and testing apparatus.

Supply air 32 is delivered to the system through regulator 33. Regulated supplies from regulator 33 are delivered as follows: supply 34 to 4-way 2-position valve 35; supply 36 to regulator 37 which serves to limit the maximum attainable pressure generated with pneumatic cylinder 10 via supply 38 to 4-way 2-position valve 39; supply 40 to pulse timer 41; supply 42 to inhibitor 43; and supply 44 to delay timer 45.

At the start of a cycle, pneumatic cylinder 9 is in the extended position and there is no air pressure on pilot 46 of inhibitor 43. This causes inhibitor 43 to deliver air at system supply pressure to port 47 and to lines 48 and 49. The air pressure at pilot port 48 of 4-way 2-position valve 35 causes system supply pressure 34 to be directed to line 50, and line 74 to be vented, thus retracting actuator 9 and isolating a sample. In the retracted position, limit switch 15 is opened by limit tab 16, allowing air from line 51 to be delivered to pilot port 52 of pulse timer 41. Pulse timer 41 delivers system supply air to line 53 for an adjustable time period, typically 2 to 7 seconds. Pressure on pilot port 53 of 4-way 2-position valve 39 directs supply pressure to lines 54 and 55, and vents line 60. This causes actuator 10 to extend and to pressurize the trapped sample. Pressure on line 55 closes switch 56, thereby sending electrical signal 57 to microprocessor 14. Microprocessor 14 is continuously reading electrical information 58 and 59 from pressure transducer 12 and position sensor 13 (FIG. 1). Prior to receiving signal 57, microprocessor 14 interprets the pressure transducer and position sensor signals as initial values. While receiving signal 57, microprocessor 14 interprets the pressure transducer and position sensor signals as final values. When time runs out on the pulse timer 41, line 53 vents, valve 39 returns by spring action, lines 54 and 55 vent, and line 60 pressurizes. This causes actuator 10 to retract. Also, with line 55 vented, switch 56 opens, signalling microprocessor 14 to calculate the entrained air content, to provide output signals 61, and to return to interpreting the pressure transducer and position signals as initial values.

In the preferred embodiment, switch 56 is a single-pole single-throw pneumatic to electrical switch.

The discharge of the isolated sample due to the extension of actuator 9 is initiated by the same pressure signal 47 from inhibitor 43, which started the cycle. Air passing through line 49 passes through adjustable timer 62 which discharges through line 63, check valve 64, and line 65. Supply 65 pressurizes accumulator 67 through line 66. Line 68 provides a continuous bleed of line 65 and accumulator 67 by means of bleed valve 69 and vent 70. While timer 62 is open, accumulator 67 fills with air. When timer 62 shuts off, check valve 64 ensures no back flow of air through timer 62, and pressure in isolated accumulator 67 is slowly vented through bleed valve 69. Open time on timer 62, size of accumulator 67, and bleed rate by valve 69 control the amount of time that pressure is maintained on pilot port 71 of delay timer 45. With port 71 pressurized, delay timer 45 remains closed for an adjustable time, typically 2 to 7 seconds. At the end of the delay time, air is allowed to pass from supply 44 to line 72. This puts pressure on pilot port 46 of inhibitor 43 causing inhibitor 43 to shut off supply to line 47. With pilot air removed from port 48 and added to port 73 of 4-way 2-position valve 35, line 74 is pressurized, line 50 is vented, and the sample pistons are extended into the process fluid by actuator 9. This condition prevails as long as pressure remains on pilot port 71 of delay timer 45. When the pressure in accumulator 67 is vented below a minimum value, delay timer 45 shuts off and vents line 72 and pilot port 46 of inhibitor 43. The cycle thus repeats at this stage.

Time cycles can be adjusted through any ranges and are limited only by the constraint that the sample must remain isolated while actuator 10 completes its cycle. Thus, when configured as described, delay timer 45 controls the amount of time that the sample is isolated (piston retracted), so that the delay time for delay timer 45 must be greater than pulse time for pulse timer 41, which controls the cycle time of actuator 10. In the preferred embodiment, the time between complete system cycles is controlled by the combination of timer 62, accumulator 67, and bleed 69. In an alternate embodiment, reversal of lines 74 and 50 on actuator 9 will cause the delay timer 45 to regulate the extended time rather than the retracted time of the sample pistons, so that the time delay for pressure bleed in the combination timer 62, accumulator 67, and bleed 69 now must be greater than the pulse timer 41 setting.

The minimum length of time for operation of pulse timer 41 is governed by the movement time of actuator 10. A pulse time of 2 seconds is sufficient. Longer pulse times provide no additional value except to allow for detection of any leakage by the seals. Longer pulse times can be routinely provided, but to minimize costs a practical limit is 7 seconds.

In the preferred embodiment, the cycle is designed to maximize the sample piston extended time. In an alternate embodiment, reversal of lines 74 and 50 on actuator 9 allows the retraction time to be maximized. The actual operating mode can be selected on the basis of process conditions. For example, excessive abrasive wear of piston 6 (FIG. 1) might occur in some process fluids in which case retraction time should be maximized. The total cycle time is limited on the high frequency end to about 4 seconds due to pneumatic component response times. Use of higher speed actuators can lower this cycle time. Cycle time on the high frequency end is also limited by seal wear and is dependent upon the process conditions. Thus, the slowest cycle time which still allows tracking of process dynamics is desirable. Cycle times much greater than 1 hour and down to 4 seconds are attainable. In typical pulp and paper industry applications, desirable cycle times are 1 to 15 minutes.

The apparatus in this disclosure is operated by pneumatic logic as just described. Clearly, other timing mechanisms are feasible. Thus, for example, microprocessor 14 could be expanded to provide electro-pneumatic control by removing all pneumatic logic components and replacing pneumatically operated 4-way 2-position valves 35 and 39 with electrically operated pneumatic valves.

I claim:

1. Apparatus for determination of an entrained gas-phase component in a liquid sample which comprises:
   a cylinder having a sample receiving end;
   a first piston rod axially located within the cylinder, said first piston rod having mounted thereon a spaced apart first piston and sealing plate, the spacing of said first piston and sealing plate being less than the length of the cylinder, said first piston having a sample contacting face and an opposite face and being sized to fit snugly within the cylinder to provide a liquid seal, the sealing plate being of greater diameter than the cylinder;
   a first actuating means coupled to said first piston rod to translate said first piston within the cylinder and move the sealing plate into and out of sealing relationship with the sample receiving end of the cylinder, so that when in sample receiving position the sample contacting face of said first piston is positioned flush with the sample receiving end of the cylinder and in sample testing position the sealing plate is tightly engaged against the sample receiving end;
   a second actuating means mounted on said opposite face of said first piston and moveable therewith, the second actuating means having a second piston rod passing through said first piston in a liquid sealed relationship so as to be translatable toward or away from the sealing plate;

a pressure transducer means mounted to indicate pressure within a volume between said first piston and said sealing plate; and a transducer responsive to the linear position of said second rod on said second actuating means, whereby the sample receiving end of the cylinder may be located in a liquid to be sampled with said first piston and sealing plate being in sample receiving position, a sample drawn into the cylinder by retracting said first piston so that a sample is retained in the cylinder between the sealing plate and sample contacting face of said first piston, the second piston rod of the second actuating means then being actuated into the contained sample so that any entrained gas is compressed, the volume of the entrained gas being determined by noting the change in pressure and change in sample volume as indicated by the change in linear position of said second actuating means piston rod.

2. The apparatus of claim 1 in which either of the first and second actuating means are fluid actuated cylinders.

3. The apparatus of claim 1 in which either of the first and second actuating means are geared electric motors.

4. The apparatus of claim 1 in which the transducer responsive to the linear position of the second actuating means piston rod is a linear potentiometer.

5. The apparatus of claim 1 in which the transducer responsive to the linear position of the second actuating means piston rod is a linear variable differential transformer.

6. The apparatus of claim 1 further including timing means for automatically sequencing both actuating means.

7. The apparatus of claim 6 which further includes a microprocessor to calculate the percentage of entrained gas phase by entering pressure change and volume change into a Boyle's Law equation and solving the equation.

8. The apparatus of claim 1 in which the pressure transducer means is mounted on the sample contacting face of the piston.

* * * * *